US005660821A

United States Patent [19]

Birbara et al.

[11] Patent Number: 5,660,821
[45] Date of Patent: Aug. 26, 1997

[54] EXTENDED-RELEASE CHEMICAL FORMULATION IN TABLET FORM FOR URINE PRETREATMENT

[75] Inventors: Philip J. Birbara, Windsor Locks; Harold T. Couch, Canton; Joseph E. Genovese, East Granby; Donald W. Rethke, Granby, all of Conn.

[73] Assignee: United Technologies Corporation, Hartford, Conn.

[21] Appl. No.: 499,285

[22] Filed: Jul. 7, 1995

[51] Int. Cl.$^6$ .................................................. A01N 25/34
[52] U.S. Cl. ................ 424/76.7; 424/76.5; 424/76.6; 424/76.8; 424/408; 424/470; 510/253; 510/363; 510/367; 510/475; 514/960; 514/961
[58] Field of Search ............................ 424/76.1, 76.5, 424/76.6, 76.7, 76.8, 408, 464, 465, 468, 470; 4/309; 510/108, 109, 191, 193, 245, 247, 253, 363, 367, 375, 446, 475, 488; 514/960, 961

[56] References Cited

U.S. PATENT DOCUMENTS

| | | | |
|---|---|---|---|
| 4,132,753 | 1/1979 | Blichare et al. | 264/462 |
| 4,155,868 | 5/1979 | Kaplan et al. . | |
| 4,272,393 | 6/1981 | Gergely . | |
| 4,647,458 | 3/1987 | Ueno et al. . | |
| 4,749,411 | 6/1988 | Chapin . | |
| 4,863,445 | 9/1989 | Mayhan et al. | 604/317 |
| 5,019,346 | 5/1991 | Richter et al. . | |
| 5,278,036 | 1/1994 | Kobayashi et al. | 430/465 |
| 5,313,672 | 5/1994 | Luedtke et al. . | |
| 5,328,633 | 7/1994 | Hasting et al. | 252/181 |
| 5,384,062 | 1/1995 | Eoga et al. . | |
| 5,398,347 | 3/1995 | Luedtke et al. . | |

OTHER PUBLICATIONS

Donaghy, Leonard S., "Tablet Binders", Drug and Cosmetic Industry, Published in Sep. 1958, vol. 83, No. 3, pp. 304, 377, 378.

Ullmann's Encyclopedia of Industrial Chemistry, Fifth, Completely Revised Edition, Elvers et al., Editors, vol. A19, Published 1991, pp. 251-257.

Evrard et al., "Melt Granulation with a New Laboratory High-Shear Mixer", Cong. Int. Technol. Pharm., vol. 3, pp. 187-196 (1992).

*Primary Examiner*—Melvyn I. Marquis
*Assistant Examiner*—Robert H. Harrison
*Attorney, Agent, or Firm*—Mary R. Bonzagni, Esq.; Holland & Bonzagni, P.C.

[57] ABSTRACT

The present invention provides water-soluble, extended-release chemical formulations, in tablet form, for urine pretreatment, that require minimal, if any, use of a binder component, yet are non-dusting, pliable, structurally strong, and not weakened by exposure to aqueous streams. The present invention also provides a simple and reliable method for controlled dispensing of such tableted formulations into a liquid stream that is particularly advantageous for use in micro-gravity environments, such as spacecraft urinal systems.

12 Claims, No Drawings

EXTENDED-RELEASE CHEMICAL FORMULATION IN TABLET FORM FOR URINE PRETREATMENT

FIELD OF THE INVENTION

The present invention relates generally to extended-release chemical formulations. The present invention more particularly relates to water soluble, extended-release chemical formulations, in tablet form, for urine pretreatment, methods for preparing same, and to a method for controlled dispensing of such tableted formulations.

BACKGROUND OF THE INVENTION

Conventional toilet bowl cleaners for home or commercial use are typically composed primarily of sodium bisulfate with minor amounts of detergent, fragrance, and corrosion inhibitor. These cleaners optionally contain a small amount of a strong oxidant such as OXONE® monopersulfate compound and serve the function of soil and stain removal.

Conventional toilet bowl cleaners may take the form of: tablets that are placed in the bottom of urinals or tanks; liquids that are dispensed directly into toilet bowl or urinal water; and gels or cakes that are hung over the side of a toilet bowl or tank and that slowly dissolve when in contact with flush or tank water.

In spacecraft urinal systems, where urine is collected and stored over long periods of time, the pretreatment of urine is of eminent importance. It has been found that pretreatment serves to increase the reliability of such systems and serves to reduce the amount of maintenance time for cleaning and repairing system hardware. In particular, pretreatment of urine is required in spacecraft urinal systems to control odors, fix urea, and control microbial growth. In addition, pretreatment is required to reduce or eliminate fouling of the hardware and plumbing with urine precipitates and thereby assure long term use of urine collection equipment.

Typically urine contains about 96 percent water and about 4 percent solids in solution. About half of the solids consist of urea, $(NH_2)_2CO$, while the remainder of the solids include chloride, sodium, potassium, nitrogen, ketosteroids, phosphate, sulfur, ammonia, creatinine, and uric acid. Without some form of pretreatment, many of the constituents of urine will decompose at room temperature and will become contaminated with bacteria, which will result in further decomposition. In particular, urea decomposes resulting in the formation of ammonia and carbon dioxide, and a significant amount of solids precipitate out of solution resulting in the fouling of urine collection equipment. Additionally, the evaporation of water in urine, resulting from air entrainment therein, facilitates the precipitation of urine salts.

The pretreatment of urine for long term storage in microgravity environments, such as those found in spacecraft urinal systems, present numerous technical hurdles however. Spacecraft urine collection equipment or devices employ little or no flush water. Chemicals, in powder form, are not easily metered into a fluid stream in such micro-gravity environments and many pretreatment chemicals in solution degrade over time. Moreover, weight and volume penalties associated with any pretreatment scheme for spacecraft applications must be minimized.

Known methods of pretreating urine in such micro-gravity environments include: mixing solid OXONE® and liquid sulfuric acid with an aqueous medium for liquid injection into a urine stream; and dispensing water soluble organic acids in powder or tablet form, via mechanical means.

Such pretreatment methods are presently employed only on extended duration (e.g., up to 30 days) and long duration (e.g., greater than 30 days) space flights. Present experience has revealed however that pretreatment is necessary on short duration (e.g., up to 2 weeks) flights as well. In particular, during a recent Shuttle flight, significant deposits of urine solids were discovered upstream of a liquid collection storage tank. It was recognized that these deposits can lead to premature failure of the urinal system.

Known micro-gravity pretreatment methods are problematic however in that the use of liquid sulfuric acid presents severe handling problems which include containment and corrosion problems. In addition the efficiency of OXONE® in solution degrades significantly over time. Moreover, dispensing methods presently require dual injection systems (i.e., mixing and injecting one portion of the pretreatment chemicals up-stream of a urine separator device and the other portion down-stream of the device) which contribute to complexity, increased maintenance and reliability concerns.

Further to the above, U.S. Pat. No. 5328633 to Hasting et al. discloses soluble, extended-release tablets for removing and preventing plaque formation that are placed into a system, such as a ship's collection, holding, and transfer system. Once in the system, the tablets maintain the pH of the system at an acidic state that reportedly prevents the precipitation and subsequent build up of a plaque of insoluble salts and that reportedly dissolves existing plaque. The tablets are formed by compression molding techniques (see, Column 4, lines 55 to 68) and are made up of: 50 to 95 wt% of a benign organic acidic agent (e.g., citric acid); and 5 to 50 wt% of an extended-release binder comprised of poly(ethylene glycol) (MW=4,000 to 20,000 grams/mole) and poly(ethylene oxide) (MW=100,000 to 5,000,000 grams/mole). However, Examples 1 to 17 of Hasting et al. use binder concentrations of 25 to 30 wt%, which would contribute to weight and volume penalties in spacecraft applications. Moreover, it is submitted that binder concentrations of less than or equal to 10 wt% would not serve to adequately bind the composition of Hasting et al.

It is therefore an object of the present invention to provide an extended-release chemical formulation in tablet form that requires minimal, if any, use of a binder component yet is non-dusting, pliable, structurally strong, and not weakened by exposure to aqueous streams.

It is a further object to provide an extended-release chemical formulation that serves to prevent urine solids from precipitating and depositing on internal collection and storage tank surfaces, that aids in the reduction of the transfer of urine odors, and that stabilizes urine for long term storage.

It is yet a further object of the present invention to provide a simple and reliable method for controlled dispensing of an extended-release chemical formulation into a liquid stream that requires little or no maintenance and that avoids the problems associated with mechanical injection means.

SUMMARY OF THE INVENTION

The present invention therefore provides a water soluble, extended-release chemical formulation, in tablet form, for controlling and preventing microbial growth and/or for controlling and preventing precipitation of solids in and transfer of odorous gases from urine, which comprises:

a. a biocide; and/or b. an organic acid or an acid salt; and c. from about 1.5 to about 10% by weight of an extended-release binder, where the biocide is an acid oxidizing compound selected from the group including monopersulfate compounds, copper sulfate, silver nitrate, and mixtures thereof, where the organic acid is selected from the group including citric, oxalic and maleic acids, and mixtures thereof, where the acid salt is selected from the group including potassium bisulfate, sodium bisulfate, cupric chloride, silver nitrate, and mixtures thereof, where the binder is comprised of: at least one polyol having an average molecular weight ranging from about 600 to about 20,000 grams/mole; and, optionally, polyethylene oxide, and where, the chemical formulation is prepared by a method comprising:
 preparing a mixture made up of: the biocide; and/or, the organic acid or the acid salt; and the binder;
 heating the prepared mixture to a temperature of from about 45° C. to about 70° C.;
 cooling the heated mixture to ambient temperature; and pressing the cooled mixture into at least one tablet.

The present invention also provides a water soluble, extended-release chemical formulation, in tablet form, for controlling and preventing precipitation of solids in and transfer of odorous gases from urine and, optionally, for controlling and preventing microbial growth, which comprises: an organic acid or an acid salt; and up to about 10% by weight of an extended-release binder, where the organic acid, the acid salt, and the binder are defined as set forth above, and where the formulation is prepared by a method comprising:
 heating the organic acid or the acid salt, alone or in combination with the binder, to a temperature sufficient to melt the acid or the salt to form a melt; optionally, adding the binder to the melt;
 pouring the melt into at least one mold; and
 cooling the melt, contained in the mold(s), to form at least one tablet.

The present invention further provides a method for controlled dispensing of the above-referenced formulations into a liquid stream whereby the tableted formulations control and prevent microbial growth and/or control and prevent precipitation of solids in and transfer of odorous gases from urine, where the method comprises:
 securing the extended-release chemical formulations within a permeable casing; and
 mounting the permeable casing, containing the tableted formulations, in a liquid flow path leading to urine collection hardware or in the urine collection hardware.

DETAILED DESCRIPTION OF THE INVENTION

Although the present invention is particularly suited for use in micro-gravity environments it is not so limited. The present inventive formulations, in tablet form, and the present inventive method for controlled dispensing of such tableted formulations may be employed just as effectively in gravity environments.

The biocides of the present inventive chemical formulation are water soluble acid oxidizing compounds that serve to control odors and microbial growth. Examples of suitable biocides include monopersulfate compounds, copper sulfate, silver nitrate, and mixtures thereof. The biocide is preferably an alkali metal monopersulfate or an alkaline earth metal monopersulfate having an average particle size ranging from about 0.1 to about 0.5 millimeters (mm) and more preferably is potassium monopersulfate present in the form of a triple salt compound with potassium bisulfate and potassium sulfate (e.g., $KHSO_5 \cdot KHSO_4 \cdot K_2SO_4$). This triple potassium salt is available from E. I. DuPont DeNemours & Co., Inc. in a 2:1:1 mole ratio under the trade designation OXONE® monopersulfate compound.

The organic acids and acid salts of the present invention serve to acidify the urine stream being pretreated thereby reducing the potential for urine solids depositing on internal surfaces and simultaneously diminishing the rate of release of odorous gases, such as ammoniacal gases, from the urine stream. Examples of suitable organic acids include citric, oxalic, and maleic acids, and mixtures thereof. Examples of suitable acid salts include potassium bisulfate, sodium bisulfate, cupric chloride, silver nitrate and mixtures thereof. It is preferred that the organic acids and the acid salts have an average particle size ranging from about 0.2 to about 0.5 mm and from about 0.1 to about 0.5 mm, respectively.

The extended-release binder of the present inventive chemical formulations serves to bind the formulation components and to effect the rate at which the tableted formulation dissolves. The binder is preferably present in an amount up to about 10% by weight, and more preferably, is present in an amount ranging from about 1.5 to about 10% by weight, based on the total weight of the formulation. Preferred binders have average particle sizes ranging from about 0.1 to about 0.5 mm and are comprised of: at least one polyol having an average molecular weight ranging from about 600 to about 20,000 grams/mole and, preferably, from about 4,000 to about 10,000 grams/mole; and, optionally, polyethylene oxide. The rate of chemical release to a urine stream is enhanced when the average molecular weight of the binder falls within the lower end of the above-referenced range and is reduced when the average molecular weight of the binder falls within the upper end of the range.

It is preferred that polyethylene oxide, having an average molecular weight ranging from about 300,000 to about 600,000 grams/mole, be employed with the polyol of the above-referenced binder when the inventive formulation is intended for use in gravity environments. The polyethylene oxide has been found to further retard the rate at which the tableted formulation dissolves in an aqueous solution or stream. It is more preferred that the polyethylene oxide be present in an amount ranging up to about 5% by weight, based on the total weight of the binder.

In addition to the components set forth above, the present inventive formulations may contain additional components that do not interfere with its urine pretreatment functions.

As will be more apparent from the discussion detailed below the chemical formulations of the present invention are preferably prepared by a method that employs compression molding techniques. However, the chemical formulations of the present invention, that do not employ a biocide, are also preferably prepared by a casting method.

One preferred embodiment of the present invention is a water soluble, extended-release chemical formulation, in tablet form, which comprises:
 a. from about 10 to about 75% by weight, and preferably, from about 40 to about 60% by weight, of a biocide comprising a triple potassium salt with the formula $KHSO_5 \cdot KHSO_4 \cdot K_2SO_4$;
 b. from about 10 to about 75% by weight, and preferably, from about 40 to about 60% by weight, of an acid salt comprising potassium bisulfate; and
 c. from about 1.5 to about 5.0% by weight, and preferably, from about 1.5 to about 2.5% by weight, of a binder comprising polyethylene glycol having an average molecular weight ranging from about 4,000 to about 10,000 grams/mole, where the sum of components a, b and c total 100% by weight.

Another preferred embodiment of the present invention is a formulation which comprises:

a. from about 5 to about 70% by weight, and preferably, from about 10 to about 50% by weight, of a biocide comprising a triple potassium salt with the formula $KHSO_5 \cdot KHSO_4 \cdot K_2SO_4$; and/or b. from about 25 to about 90% by weight, and preferably, from about 40 to about 80% by weight, of an organic acid comprising citric acid; and c. from about 2 to about 10% by weight, and preferably, from about 4 to about 8% by weight, of a binder comprising polyethylene glycol having an average molecular weight ranging from about 4,000 to about 10,000 grams/mole, where the sum of the components total 100% by weight.

The above-referenced chemical formulations are preferably prepared by a method comprising: preparing a mixture made up of: the biocide; and/or, the organic acid or the acid salt; and the binder; heating the prepared mixture to a temperature of from about 45° C. to about 70° C.; cooling the heated mixture to ambient temperature; and pressing the cooled mixture into at least one tablet. The cooled mixture is preferably pressed into tablets using compression molding techniques where the mixture is placed in at least one mold and a pressure of from about 30 to about 140 megapascals (MPa), and preferably, from about 80 to about 125 MPa, is applied to the mixture contained in the mold(s), for up to about 30 seconds, to form at least one tablet.

As will be readily recognized by those skilled in the art, the particle sizes of the formulation components and the pressures applied during compression molding also affects the rate of dissolution of the tableted formulation.

It has been observed that when the prepared mixture is heated the salts agglomerate and take on a rather uniform and coarser grain size. While not intending to be bound by theory, it is believed that the observed agglomeration advantageously affects the bonding and resulting structural integrity observed.

Formulations of the present invention that do not employ a biocide are also preferably prepared by a casting method comprising: heating the organic acid or the acid salt, alone or in combination with the binder, to a temperature sufficient to melt the acid or the salt to form a melt; optionally, adding the binder to the melt; pouring the melt into at least one mold; and cooling the melt, contained in the mold(s), to form at least one tablet. Tablets prepared according to this method are denser and as a result dissolve at a rate slower than tablets prepared by the method employing compression molding techniques. Moreover and surprisingly, it has been found that binder-free cast tablets dissolve at a slower rate than cast tablets employing a binder.

In a preferred casting method the organic acid is heated to a temperature of from about 50° C. to about 250° C and, more preferably, to a temperature of from about 100° C. to about 200° C. In another preferred casting method the acid salt is heated to a temperature of from about 100° C. to about 400° C. and, more preferably, to a temperature of from about 120° C. to about 250° C.

Tablets made from the chemical formulations of the present invention are preferably stored in a cool, dry environment, with or without a desiccant.

The method for controlled dispensing of the inventive tableted formulations into a liquid stream, such as a urine stream, basically comprises: securing the tableted formulations within a permeable casing; and mounting the permeable casing, containing the tableted formulation, in a liquid flow path leading to urine collection hardware or within urine collection hardware. As will be readily evident to those skilled in the art, the present inventive method may be employed in both gravity and micro-gravity applications.

In a preferred method a plurality of tablets are inserted into a hydrophilic, permeable, cylindrically-shaped casing and then each tablet is separately encased by tying off a portion of the casing located between and/or next to each tablet. Examples of suitable hydrophilic, permeable casing materials include non-woven polyester and cellulosic membrane materials.

The following examples are presented for illustration purposes only and are not intended to limit the broad scope of the invention detailed herein.

WORKING EXAMPLES

In the working examples set forth below specimens of preferred embodiments Of the present inventive formulations were prepared. The prepared specimens were then tested for rate and manner of dissolution. In addition, tablets were prepared in accordance with the teachings of U.S. Pat. No. 5328633 to Hasting et al. The following components were used:

PEG 1450 —polyethylene glycol powder, average molecular weight 1450, average particle size 0.2 to 0.4 mm, obtained from J. T. Baker, Inc., 222-T Red School Lane, Phillipsburg, N. J. 08865.

PEG 8000 —polyethylene glycol powder, average molecular weight 8000, average particle size 0.2 to 0.4 mm, obtained from J. T. Baker, Inc.

CITRIC ACID —citric acid anhydrous powder, average particle size 0.2 to 0.4 mm, available from J. T. Baker, Inc.

OXONE —a triple potassium salt in powder form, average particle size 0.1 to 0.4 mm, available from E. I. DuPont DeNemours & Co., Inc. under the trade designation OXONE.

POTASSIUM BISULFATE —potassium bisulfate powder, average particle size 0.2 to 0.4 m/n, available from J. T. Baker, Inc.

EXAMPLE 1

Example 1 was prepared as follows: a quantity of 3 grams of PEG 1450 was weighed out in a 100 milliliter (ml) glass beaker while a quantity of 27 grams of CITRIC ACID was weighed out in a 200 ml glass beaker; the beaker containing the PEG 1450 was then heated to about 50° C. on a hot plate to melt the PEG 1450 while the beaker containing the CITRIC ACID was heated to about 150° C. on a hot plate to melt the CITRIC ACID. The volume of the CITRIC ACID was reduced more than 5 fold upon liquidification. The liquid PEG 1450 was then added to the liquid CITRIC ACID and the liquids thoroughly mixed with a glass rod for about one minute while maintaining the temperature of the resulting mixture at 150° C. by heating on a hot plate. Upon contact of the liquid PEG 1450 with the liquid CITRIC ACID a small quantity of water vapor was observed evolving from the mixture. The liquid PEG 1450/CITRIC ACID mixture was then poured into an aluminum foil weighing container measuring 5 centimeters (cm) in diameter. The mixture was then solidified by cooling to ambient temperature and the solidified mixture removed from the aluminum container by peeling back the aluminum foil. The solidified mixture was uniform in texture, non-dusting and slightly flexible and pliable. A specimen weighing 2.8 grams was then obtained from the solidified mixture and tested for rate and manner of dissolution as set forth below.

The specimen was positioned about 5 cm from a tapered nozzle faucet in the path of dripping tap water, flowing at a rate of 150 to 200 ml/minute. The dripping tap water was collected in a 4 liter graduated cylinder and the pH of the collected water measured with each 500 ml increment collected. pH measurements ranged from 1 to 3. Approximately 3 liters of water were required to totally dissolve the specimen. The specimen was lightly impacted with a glass rod during dissolution. The specimen did not break apart and dissolved in a uniform manner.

EXAMPLE 2

Example 2 was prepared as follows: a quantity of 0.3 grams of PEG 1450 and a quantity of 9.7 grams of OXONE were separately weighed in 200 ml glass beakers. The beaker containing the PEG 1450 was then heated to about 50° C. on a hot plate to melt the PEG 1450. The OXONE was then added to the liquid PEG 1450 and thoroughly mixed with a glass rod for about 3 minutes. The OXONE was observed to have a slightly agglomerated appearance. The resulting PEG 1450/OXONE mixture was then heated to 60° C. in a microwave oven set at 700 watts for about one minute and stirred again with a glass rod for 60 seconds. The mixture was then cooled to ambient temperature. A quantity of 4 grams of the cooled mixture was then poured into a cavity of a mold measuring 1.27 cm in diameter which was then inserted into a Carver Laboratory Press, Model C, manufactured by Fred S. Carver, Inc., P.O. Box 544, Dept. Z, Wabash, Ind. 46992. A pressure of 125 MPa was then applied to the mixture contained in the mold for 1 minute and a 1.52 cm long rod was formed thereby.

The specimen rod was submerged in 200 ml of water. Approximately 5 hours were required to totally dissolve the specimen rod. Probing of the specimen during dissolution indicated that the structural integrity of the rod was not adversely affected by the dissolution process. The specimen dissolved in a uniform manner.

EXAMPLE 3

Example 3 was prepared as follows: a quantity of 50 grams of OXONE, 165 grams of POTASSIUM BISULFATE and 3.0 grams of PEG 8000 were separately weighed in 150 ml glass beakers. The weighed components were then placed in a capped 250 ml. polyethylene bottle and mixed by manually shaking and rotating the bottle for 60 seconds. The mixture was then heated for 5 minutes to 60° C. in a microwave oven, set at 700 watts. The heated mixture was then cooled to ambient temperature. A quantity of 5 grams of the cooled mixture was then poured into a cavity of a mold measuring 1.27 cm in diameter which was then inserted into a Carver Laboratory Press. A pressure of 125 MPa was then applied to the mixture contained in the mold for 1 minute and a 1.52 cm long rod was formed thereby.

The specimen rod was submerged in 200 ml of water. Approximately 3 hours were required to totally dissolve the specimen rod. The structural integrity of the specimen was maintained during the dissolution process. The specimen dissolved in a uniform manner.

EXAMPLES 4 AND 5 AND COMPARATIVE EXAMPLES C1 TO C6

Examples 4 and 5 were prepared as follows: a quantity of 10 grams of CITRIC ACID and 1 gram. of PEG 8000 were separately weighed in aluminum weighing containers measuring 5 cm in diameter. The weighed components were then placed in a 50 ml polyethylene bottle and mixed by shaking and stirring with a glass rod for 60 seconds. The resulting mixture was then heated in a microwave oven set at 500 watts for 4 minutes. The mixture was removed at 1 minute intervals from the microwave oven, during heating, and shaken and stirred for 30 seconds. The mixture was cooled to ambient temperature and a quantity of 3 grams of the cooled mixture was then placed in two molds, each measuring 1.27 cm in diameter. The molds were then inserted into a Carver Laboratory Press and a pressure of 34 MPa and 138 MPa, respectively, was applied to the mixture contained in each mold for 10 seconds and two 1.5 cm long tablets were formed thereby. The tablets did not break upon release from the molds.

Comparative Examples C1 to C6 were prepared in accordance with the procedure set forth at Column 4, lines 55 to 68 of U.S. Pat. No. 5328633. In particular, Comparative Examples C1 to C6 were prepared as follows: CITRIC ACID and mixtures of CITRIC ACID and varying quantities of PEG 8000 were placed in molds measuring 1.27 cm in diameter. The molds were placed in a Carver Laboratory Press and a pressure of either 34 MPa or 138 MPa was applied for 10 seconds to the mixture contained in each mold. Brief descriptions of the tablets produced for the above-referenced examples are set forth below in TABLE 1.

TABLE 1

SUMMARY OF EXAMPLES 4 AND 5 AND COMPARATIVE EXAMPLES C1 TO C6

| Example | PEG 8000 (% by weight) | CITRIC ACID (% by weight) | Applied Pressure (MPa) | Description of Tablets Produced |
| --- | --- | --- | --- | --- |
| 4 | 10 | 90 | 34 | no breakage upon release from mold |
| 5 | 10 | 90 | 138 | no breakage upon release from mold |
| C1 | 0 | 100 | 34 | tablet broke apart, crumbled easily |
| C2 | 0 | 100 | 138 | tablet broke apart, crumbled easily |
| C3 | 10 | 90 | 34 | tablet broke apart, crumbled easily |
| C4 | 10 | 90 | 138 | tablet broke apart, crumbled easily |
| C5 | 50 | 50 | 34 | no breakage upon release from mold |
| C6 | 50 | 50 | 138 | no breakage upon release from mold |

As clearly demonstrated by the results displayed in TABLE 1 and unlike the present invention, tablets prepared according to the teachings of U.S. Pat. No. 5328633 to Hasting et al. and containing less than or equal to 10% by weight PEG 8000 crumble and break apart upon attempts to release the tablets from the molds.

Having thus described the invention what is claimed is:

1. A water soluble, extended-release chemical formulation, in tablet form, for controlling and preventing microbial growth and/or for controlling and preventing precipitation of solids in and transfer of odorous gases from urine, which comprises:

a. from about 5 to about 97% by weight of a biocide; and, optionally, b. from about 25 to about 90% by weight of an organic acid or from about 10 to about 75% by weight of an acid salt; and c. from about 1.5 to about 10% by weight of an extended-release binder, wherein said biocide is an acid oxidizing compound selected from the group consisting of monopersulfate compounds, copper sulfate, silver nitrate, and mixtures thereof, wherein said organic acid is selected from the group consisting of citric, oxalic and maleic acids, and mixtures thereof, wherein said acid salt is selected from the group consisting of potassium bisulfate, sodium bisulfate, cupric chloride, silver nitrate, and mixtures thereof, wherein said binder is comprised of: at least one polyol having an average molecular weight ranging from about 600 to about 20,000 grams/mole; and, optionally, polyethylene oxide, and wherein said chemical formulation is prepared by a method comprising:

preparing a mixture comprising: said biocide; and/or said organic acid or said acid salt; and said binder;

heating said prepared mixture to a temperature of from about 45° C. to about 70° C.;

cooling said heated mixture to ambient temperature; and pressing said cooled mixture into at least one tablet, where the sum of components A, B and C total 100% by weight.

2. The chemical formulation of claim 1, wherein said biocide is a monopersulfate compound.

3. The chemical formulation of claim 2, wherein said monopersulfate compound is a triple potassium salt with the formula $KHSO_5.KHSO_4.K_2SO_4$.

4. The chemical formulation of claim 1, wherein said organic acid is citric acid.

5. The chemical formulation of claim 1, wherein said acid salt is potassium bisulfate.

6. The chemical formulation of claim 1, wherein said binder is comprised of polyethylene glycol having an average molecular weight ranging from about 4,000 to about 10,000 grams/mole.

7. The chemical formulation of claim 6, wherein said binder further comprises up to about 5% by weight polyethylene oxide.

8. The chemical formulation of claim 1, which comprises:

a. an organic acid comprising citric acid; and b. from about 5 to about 10% by weight of a binder comprising polyethylene glycol having an average molecular weight ranging from about 4,000 to about 10,000 grams/mole.

9. The chemical formulation of claim 1, which comprises:

a. a biocide comprising a triple potassium salt with the formula $KHSO_5.KHSO_4.K_2SO_4$;

b. an acid salt comprising potassium bisulfate; and c. from about 1.5 to about 5.0% by weight of a binder comprising polyethylene glycol having an average molecular weight ranging from about 4,000 to about 10,000 grams/mole.

10. The chemical formulation of claim 1, which comprises:

a. a biocide comprising a triple potassium salt with the formula $KHSO_5.KHSO_4.K_2SO_4$;

b. an organic acid comprising citric acid; and c. from about 2 to about 10% by weight of a binder comprising polyethylene glycol having an average molecular weight ranging from about 4,000 to about 10,000 grams/mole.

11. The chemical formulation of claim 1, which comprises:

a. a biocide comprising a triple potassium salt with the formula $KHSO_5.KHSO_4.K_2SO_4$; and b. from about 2 to about 10% by weight of a binder comprising polyethylene glycol having an average molecular weight ranging from about 4,000 to about 10,000 grams/mole.

12. A water soluble, extended-release chemical formulation, in tablet form, for controlling and preventing microbial growth and for controlling and preventing precipitation of solids in and transfer of odorous gases from urine, which comprises:

a. from about 5 to about 75% by weight of a biocide;

b. from about 25 to about 90% by weight of an organic acid or from about 10 to about 75% by weight of an acid salt; and c. from about 1.5 to about 10% by weight of an extended-release binder, wherein said biocide is an acid oxidizing compound selected from the group consisting of monopersulfate compounds, copper sulfate, silver nitrate, and mixtures thereof, wherein said organic acid is selected from the group consisting of citric, oxalic and maleic acids, and mixtures thereof, wherein said acid salt is selected from the group consisting of potassium bisulfate, sodium bisulfate, cupric chloride, silver nitrate, and mixtures thereof, wherein said binder is comprised of: at least one polyol having an average molecular weight ranging from about 600 to about 20,000 grams/mole; and, optionally, polyethylene oxide, and wherein, said chemical formulation is prepared by a method wherein said binder is heated to a temperature sufficient to melt or soften said binder prior to a tablet formation step, where the sum of components A, B and C total 100% by weight.

* * * * *